(12) United States Patent
Sinderby et al.

(10) Patent No.: US 9,179,861 B2
(45) Date of Patent: Nov. 10, 2015

(54) METHOD FOR MEASURING CHANGES IN INSPIRATORY LOAD

(75) Inventors: Christer Sinderby, Toronto (CA); Jennifer Beck, Toronto (CA)

(73) Assignee: St. Michael's Hospital, Toronto (CA)

(*) Notice: Subject to any disclaimer, the term of this patent is extended or adjusted under 35 U.S.C. 154(b) by 1008 days.

(21) Appl. No.: 13/143,942

(22) PCT Filed: Jan. 15, 2010

(86) PCT No.: PCT/CA2010/000056
§ 371 (c)(1),
(2), (4) Date: Aug. 24, 2011

(87) PCT Pub. No.: WO2010/081230
PCT Pub. Date: Jul. 22, 2010

(65) Prior Publication Data
US 2011/0301482 A1    Dec. 8, 2011

Related U.S. Application Data

(60) Provisional application No. 61/193,999, filed on Jan. 16, 2009.

(51) Int. Cl.
| | | |
|---|---|---|
| A61B 5/08 | (2006.01) | |
| A61B 5/091 | (2006.01) | |
| A61B 5/0488 | (2006.01) | |
| A61B 5/087 | (2006.01) | |
| A61B 5/03 | (2006.01) | |

(52) U.S. Cl.
CPC .............. *A61B 5/091* (2013.01); *A61B 5/0488* (2013.01); *A61B 5/087* (2013.01); *A61B 5/037* (2013.01)

(58) Field of Classification Search
USPC .......................................... 600/529
See application file for complete search history.

(56) References Cited

U.S. PATENT DOCUMENTS

| | | | |
|---|---|---|---|
| 5,107,830 A | | 4/1992 | Younes |
| 5,720,709 A | * | 2/1998 | Schnall .................. 600/538 |
| 5,820,560 A | | 10/1998 | Sinderby et al. |
| 5,884,622 A | | 3/1999 | Younes |
| 6,390,091 B1 | * | 5/2002 | Banner et al. ............ 128/204.21 |
| 6,962,155 B1 | | 11/2005 | Sinderby |

(Continued)

FOREIGN PATENT DOCUMENTS

| | | |
|---|---|---|
| WO | 2007082384 A1 | 7/2007 |
| WO | 2010/022513 | 3/2010 |

OTHER PUBLICATIONS

Beck et al., "Effects of lung volume on diaphragm EMG signal Strength during voluntary contractions," J Appl Physiol., 85(3):1123-34, 1998.

(Continued)

*Primary Examiner* — Navin Natnithithadha
*Assistant Examiner* — Michael R Bloch
(74) *Attorney, Agent, or Firm* — K&L Gates LLP

(57) ABSTRACT

A method and system for measuring changes in inspiratory load of a patient's respiratory system during mechanical ventilation. The method and system calculate a first relation between a measured inspiratory airway pressure and a measured electrical activity of respiratory muscle, and a second relation between a measured inspiratory volume and the measured electrical activity. A load index is calculated from the first and second relations. Changes in inspiratory load are determined based on the load index.

7 Claims, 5 Drawing Sheets

(56) References Cited

U.S. PATENT DOCUMENTS

| | | | |
|---|---|---|---|
| 7,021,310 B1 | 4/2006 | Sinderby et al. | |
| 7,425,201 B2* | 9/2008 | Euliano et al. | 600/529 |
| 2004/0040560 A1* | 3/2004 | Euliano et al. | 128/204.23 |
| 2006/0247729 A1* | 11/2006 | Tehrani et al. | 607/42 |
| 2006/0249148 A1* | 11/2006 | Younes | 128/204.18 |
| 2008/0121231 A1* | 5/2008 | Sinderby et al. | 128/204.21 |

OTHER PUBLICATIONS

Beck et al., "Electrical Activity of the Diaphragm during Pressure Support Ventilation in Acute Respiratory Failure," American Journal of Respiratory Critical Care Med, 164:419-424, 2001.

Emeriaud et al., "Diaphragm Electrical Activity During Expiration in Mechanically Ventilated Infants", Pediatric Research, 59(5):705-10, 2006.

Beck et al., Intensive Care Medicine Annual Update 2006: Monitoring Respiratory Drive and Respiratory Muscle Unloading During Mechanical Ventilation; New York, Springer, 2006, ISBN 978-0-387-30156-3 (Print) 978-0-387-36096-7 (Online), pp. 468-474.

PCT Written Opinion of the International Searching Authority for International Application No. PCT/CA2010/000056, mailed May 6, 2010, 3 pgs.

\* cited by examiner

METHOD FOR MEASURING CHANGES IN INSPIRATORY LOAD

CROSS REFERENCE TO RELATED APPLICATIONS

This application is a national phase application under 35 U.S.C. §371 of International Application No. PCT/CA2010/000056, filed on Jan. 15, 2010, which claims priority to and the benefit of U.S. Provisional Patent Application No. 61/193,999, filed on Jan. 16, 2009, the entire disclosures of each of which are incorporated by reference herein.

FIELD

The present method and system relate to mechanical ventilation, and more particularly, to measuring changes in inspiratory load during mechanical ventilation.

BACKGROUND

Adequate delivery of mechanical ventilation in spontaneously breathing patients is difficult to determine unless information about the patient's respiratory drive and load is known.

Methods to determine the respiratory drive using electrical activity of the diaphragm EAdi (also referred to as diaphragm electomyogram EMG) have been previously proposed as well as the use of these methods to control ventilatory assist (U.S. Pat. Nos. 5,820,560; 6,962,155; 7,021,310).

Previous methods to determine the passive elastic and resistive respiratory load have also been described, for example in U.S. Pat. No. 5,884,622, to control the so-called proportional assist ventilation by applying the equation of motion as described in U.S. Pat. No. 5,107,830.

A limitation of the current methods for determining the load imposed on the patient's respiratory system resides in use of an assumption that respiratory muscles are inactive during expiration, which is not always the case.

SUMMARY

In a first aspect, the present method measures changes in inspiratory load imposed on a patient's respiratory system. For doing so, the method measures electrical activity (EAim) of at least one respiratory muscle of the patient. The method also measures an inspiratory volume (Vt), and an inspiratory airway pressure ($Paw_{occ}$) obtained during an inspiratory attempt against occluded airway. Then, the method calculates a first relation between the measured inspiratory airway pressure $Paw_{occ}$ and the measured electrical activity. The method also calculates a second relation between the measured inspiratory volume and the measured electrical activity. The method calculates a load index from the first and second relations, and determines changes in inspiratory load imposed on the patient's respiratory system in relation to the load index.

In another aspect, the present system is adapted for measuring changes in inspiratory load imposed on a patient's respiratory system. The system comprises means for measuring an electrical activity (EAim) of at least one respiratory muscle of the patient, means for measuring an inspiratory volume (Vt), and means for measuring an inspiratory airway pressure ($Paw_{occ}$) obtained during an inspiratory attempt against occluded airway. The system further comprises means for calculating a first relation between the measured inspiratory airway pressure $Paw_{occ}$ and the measured electrical activity, and means for calculating a second relation between the measured inspiratory volume and the measured electrical activity. From the first and second relation, a means for calculating calculates a load index from the first and second relations. The system also comprises means for determining changes in inspiratory load imposed on the patient's respiratory system in relation to the load index.

In yet another aspect, the present system measures changes in inspiratory load imposed on a patient's respiratory system using a measured electrical activity (EAim) of at least one respiratory muscle of the patient, a measured inspiratory volume (Vt), and a measured inspiratory airway pressure ($Paw_{occ}$). In this aspect, the system comprises a calculator for calculating a first relation between the measured inspiratory airway pressure with occluded airway and the measured electrical activity, and another calculator for calculating a second relation between the measured inspiratory volume and the measured electrical activity. Then, the system calculates a load index from the first and second relations, and calculates changes in inspiratory load imposed on the patient's respiratory system in relation to the load index.

BRIEF DESCRIPTION OF THE DRAWINGS

The foregoing and other objects, advantages and features of the present method and system will become more apparent upon reading of the following non restrictive description of an illustrative embodiment thereof, given by way of example only with reference to the accompanying drawings in which.

DETAILED DESCRIPTION

The present method and system measure changes in inspiratory load imposed on a patient's respiratory system. For doing so, the present method and system determine a dynamic load imposed on the patient's respiratory system. The method and system may be applied to any mode of artificial respiration.

More particularly, the present method and system evaluate a neural inspiratory effort of a patient's respiratory system and determine a dynamic load imposed on the patient's respiratory system. By evaluating a neural inspiratory effort, i.e. by taking into consideration the ability of the patient's inspiratory muscles to generate pleural pressure Ppl in response to a neural activation to expand the lungs, it is possible to adjust the ventilatory assist as a function of the dynamic load of the patient's respiratory system.

Figure 1:
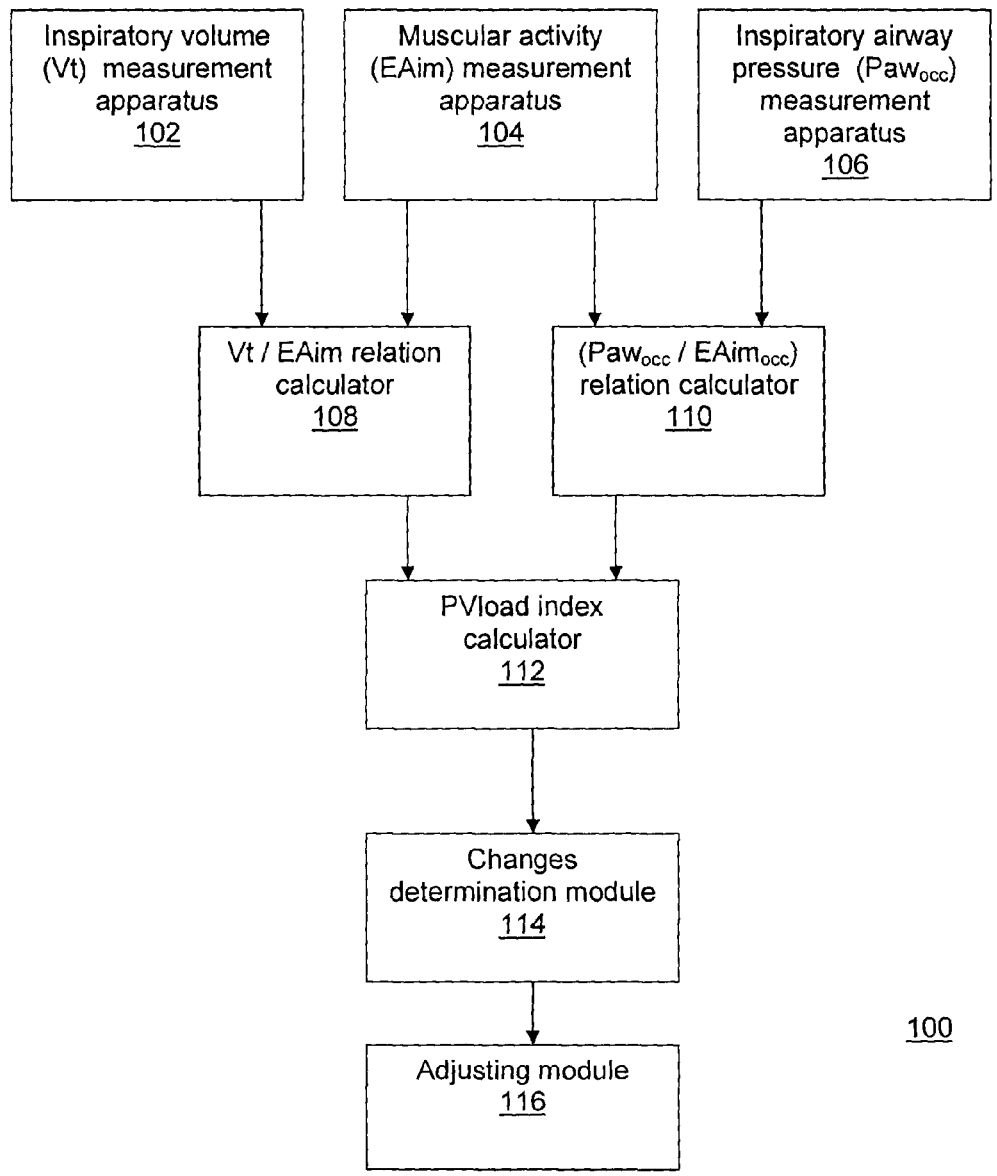
FIG. 1 is a schematic representation of a system for measuring changes in inspiratory load during mechanical ventilation in accordance with one aspect.

Reference is now made to FIG. 1, which is a schematic representation of an aspect of the present system 100 for measuring changes in inspiratory load during mechanical ventilation. The system comprises an inspiratory volume (Vt) measurement apparatus 102, an electrical inspiratory muscular activity (EAim) measurement apparatus 104 and an inspiratory airway pressure ($Paw_{occ}$) during occlusion measurement apparatus 106. The system 100 further comprises a Vt/EAim relation calculator 108 and a $Paw_{occ}$/$EAim_{occ}$ relation calculator 110. Furthermore, the system 100 comprises a PVload index calculator 112, a changes determination module 114 and an adjusting module 116.

Figure 2:
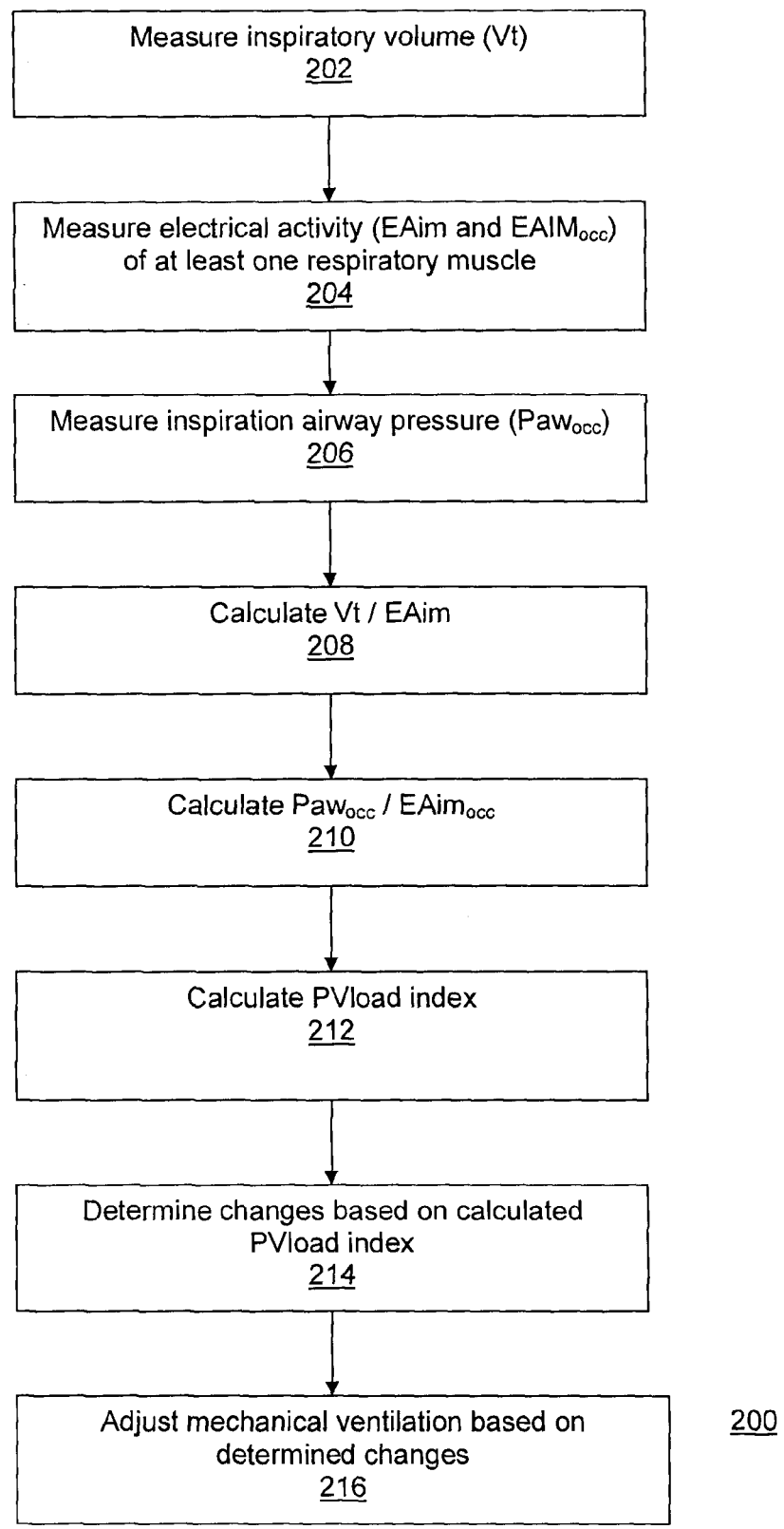
FIG. 2 is a flow diagram graphically representing a method for measuring changes in inspiratory load during mechanical ventilation.

Reference is now concurrently made to FIGS. 1 and 2, wherein FIG. 2 is a flow diagram graphically representing a method 200 for measuring changes in inspiratory load during mechanical ventilation.

Operation 202

The method 200 starts with measuring inspiratory volume Vt by means of the inspiratory volume Vt measurement apparatus 102. For measuring the inspiratory volume Vt, a pressure, flow and/or volume assist are intermittently reduced by the mechanical ventilator to a zero level or to the level of the positive end-expiatory pressure (PEEP) during one breath. The inspiratory volume Vt is measured during the patient's ventilator unassisted inspiratory effort. The inspiratory volume Vt is typically measured in liter (L).

Operation 204

The method 200 continues with measuring the electrical activity EAim of at least one respiratory muscle by means of the muscular activity EAim measurement apparatus 104. EAim is measured during the patient's ventilator unassisted inspiratory effort and can be calculated as mean, peak, area, or in other quantities to reflect inspiratory effort. The electrical activity EAim may be measured at a diaphragm (then referred specifically as EAdim), or at any other respiratory muscle of combination of muscles. The electrical activity EAim is typically measured concurrently with the inspiratory volume Vt.

Operation 206

The method 200 pursues with measuring inspiration airway pressure $Paw_{occ}$ by means of the inspiratory airway pressure $Paw_{occ}$ measurement apparatus 106. The inspiration airway pressure $Paw_{occ}$ is measured by intermittently performing inspiratory occlusions. From the onset of an inspiration while an inspiratory valve is closed, the inspiratory airway pressure $Paw_{occ}$ is measured during a part of the inspiration or during the entire inspiration. The pressure in the airway can be calculated as peak, mean, area or other quantities.

As a static esophageal pressure Pes obtained during an inspiratory occlusion coincides with the inspiratory pressure Paw measured in an airway, or respiratory circuit of the patient's respiratory system, it is possible to alternatively measure the Pes, instead of the inspiration airway pressure $Paw_{occ}$.

The inspiration airway pressure $Paw_{occ}$ is measured concurrently with corresponding electrical activity $EAim_{occ}$.

Operation 208

Then, the method 200 calculates a first relation between the inspiratory volume Vt and the measured electrical activity EAim by the Vt/EAim relation calculator 108. This first relation represents a volume generating ability of the patient's respiratory system. The first relation is thus given by the ratio Vt/EAim, measured in L/µV during an inspiration without assist from the mechanical ventilator.

Muscles other than the muscle measured can be involved in pressure generation and contribute to the inspiratory volume, but not to the EAim generation, which makes it difficult to ensure that absolute values are adequate although delivered in calibrated units. However changes in the indices described above have been demonstrated to be reliable (Beck et at Am J Respir Crit Care Med 2001; Beck et al J Appl Physiol. 1998).

Operation 210

The method 200 calculates a second relation between the inspiration airway pressure $Paw_{occ}$ and the electrical activity $EAim_{occ}$ by means of the $Paw_{occ}$/$EAim_{occ}$ relation calculator 110.

By associating the inspiratory airway pressure $Paw_{occ}$ with the neural effort required to generate the pressure, it is possible to evaluate a "static" ability of the patient's inspiratory muscles to generate pressure for a given neural output (static neuromechanical efficiency). Thus, the pressure generating ability of the measured respiratory muscle can be represented by the ratio $Paw_{occ}$/$EAim_{occ}$, during an inspiratory attempt against occlusion. The ratio between inspiratory airway pressure $Paw_{occ}$ and the $EAim_{occ}$ is calculated and expressed in cm $H_2O$/µV.

Operation 212

The method 200 calculates a load index, also identified as PVload index, by means of the PVload index calculator 112.

By dividing the ratios ($Paw_{occ}$/$EAim_{occ}$)/(Vt/EAim) [units=(cm $H_2O$/µV)/(L/µV)], it is possible to obtain a ratio between $Paw_{occ}$ and Vt, i.e. ($Paw_{occ}$/Vt) [units=cm $H_2O$/L], a measure of how much inspiratory airway pressure Paw is needed to generate a given inspiratory volume Vt, a measure representing the inspiratory load of the patient's respiratory system. A more negative PVload index (i.e. it assumes more negative values), suggests that more inspiratory airway pressure Paw is required to generate inspiratory volume Vt, i.e. the inspiratory load of the patient's respiratory system is increasing. A less negative PVload index (i.e. it assumes less negative values), suggests that less inspiratory airway pressure Paw is required to generate inspiratory volume Vt, i.e. the inspiratory load of the patient's respiratory system is decreasing.

The PVload index cannot be used unless the patient is breathing on his/her own i.e. that the patient generates an inspiratory volume without ventilatory assist and that he/she generates a negative pressure deflection during an airway occlusion occurring when inspiring. With regards to inspiratory effort, the PVload index is effort independent i.e. it does not matter if the inspiratory effort is large or small since a large effort (high EAim) would result in more negative pressure deflection ($Paw_{occ}$) during occlusion and higher volume (Vt) during the unassisted breath compared to low efforts with lower EAdi.

Figure 3:
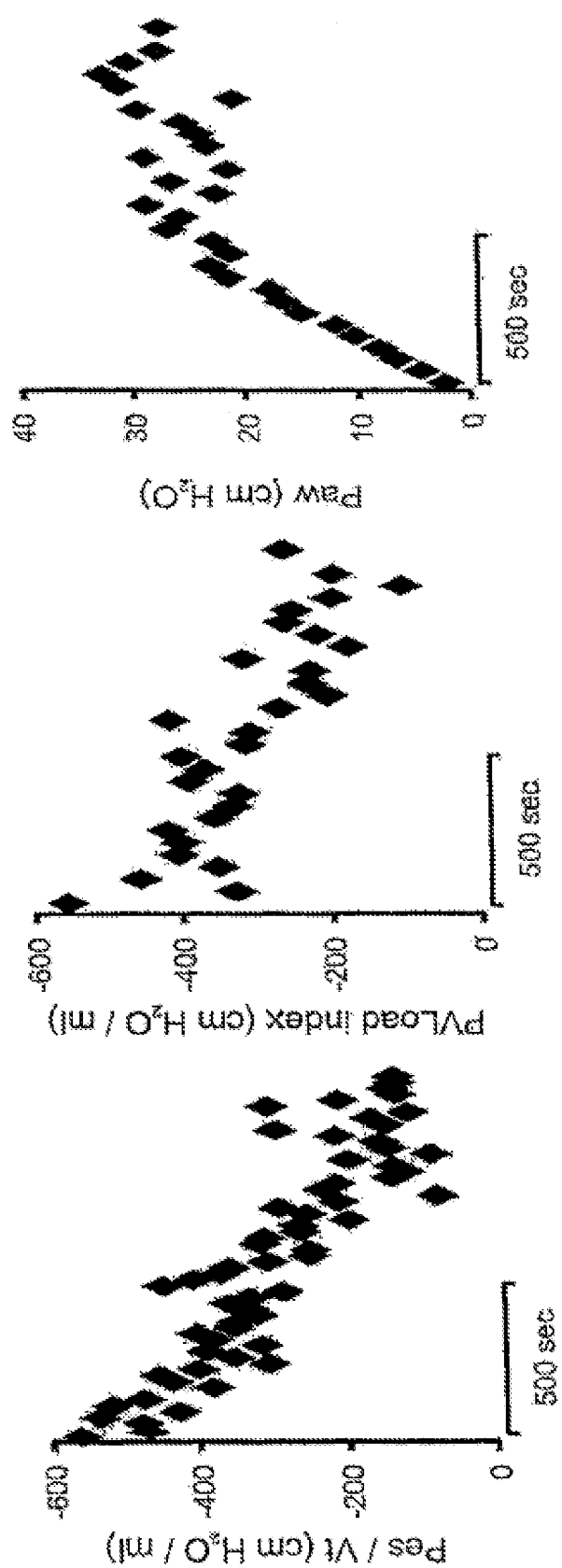
FIG. 3 are graphs of an estimated PVload index and a measured equivalent Pes/Vt ratio during ramp increase of inspiratory unloading by delivered airway pressure (Paw) and during neurally adjusted ventilatory assist.

Reference is now further concurrently made to FIG. 3, which shows graphs representing an estimated PVload index and a measured equivalent Pes/Vt ratio during ramp increase of delivered airway pressure (Paw), i.e. inspiratory unloading, with neurally adjusted ventilator assist such as described in U.S. Pat. No. 5,820,560, and a measured inspiratory load (Pes/Vt).

To identify time dependent inspiratory load components, the PVload index can be divided by Ti, the duration of the unassisted breath, as follows: ($Paw_{occ}$/$EAim_{occ}$) (Vt/EAim)/Ti.

Operation 214

The method 200 determines changes based on calculated PVload index by means of the changes determination module 114.

The division by Ti of the PVload index adds information related to time dependent (resistive) load components during the inspiration and referred to as $PVload_R$. If the $PVload_R$ index is more negative the inspiratory load is increasing and vice versa.

In order to incorporate the time dependent component to the PVload index, the duration Ti of the unassisted breath can be incorporated by multiplying it to the PVload index as follows: $(Paw_{occ}/EAim_{occ})/(Vt/EAim)*Ti$. This multiplication makes it possible to determine the integrated inspiratory load per breath and the resulting PVload index will be referred to as $PVload_{breath}$. If the $PVload_{breath}$ index is more negative the inspiratory load per breath is increasing and vice versa.

To evaluate the ischemic fatigue related components of the inspiratory load imposed on the patient's respiratory system, the inspiratory load can be multiplied by the contraction duty cycle (that is the duration Ti divided by the total time for the ventilator unassisted breath cycle) referred to as $PVload_{dc}$. If the $PVload_{dc}$ index is more negative the probability for ischemic fatigue is increasing and vice versa.

To establish a measure per minute, any of the above indices can be multiplied by the respiratory rate. If the values of the indices are more negative the inspiratory load and probability of ischemic fatigue are increasing.

Any of the above indices can be used alone or in combination to determine changes in inspiratory load during inspiration.

An example of such a determination of changes is as follows:

If measured regularly, the PVload index (or any of the other variations of this index as described above) will indicate changes in patient's inspiratory load. This information is of value for the user (caregiver) to evaluate effect of a treatment or to determine if changes in ventilatory assist are required.

For automatic application, at frequent time intervals:
1) The calculator 108 calculates the ratio Vt/EAim, wherein Vt and EAim are measured in the mechanical ventilator during an unassisted inspiration. The calculator 108 stores the calculated ratio Vt/EAim.
2) The calculator 110 calculates the ratio $Paw_{occ}/EAim_{occ}$, wherein $Paw_{occ}$ and $EAdim_{occ}$ are measured in the mechanical ventilator during a patient's occluded inspiratory effort. The calculator 110 stores the value of the ratio $Paw_{occ}/EAim_{occ}$.
3) The calculator 112 calculates the PVload index as the ratio $(Paw_{occ}/EAim_{occ})/(Vt/EAim)$ and stores the value of this PVload index.
4) The calculated PVload index is displayed on a monitor over time such that the trend can be visualized.
5) The changes determination module 114, which could for example be a comparator, compares the old (previous) PVload index value with the new (latest) PVload index value (also a regression analysis of a number of PVload values could be used) to determine if the PVload index values are increasing or decreasing.
6) An alarm implements a user-set limit to changes in the PVload index. If the old (preceding) PVload index is more negative than the new (latest) PVload index by a value that is larger than the user-set limit, the alarm triggers to indicate to the user aware that the inspiratory load imposed on the patient's respiratory system is decreasing e.g. the patient may need a lower level of ventilatory assist.
7) If the old (preceding) PVload index is less negative than the new (latest) PVload index by a value larger than the user-set limit, an alarm triggers to indicate to the user that the inspiratory load imposed on the patient's respiratory system is increasing e.g. the patient may need a higher level of ventilatory assist.

This example of monitoring may be applied to any of the above described variations of the PVload index.

Operation 216

The method 200 adjusts mechanical ventilation based on the determined changes, by the adjusting module 116.

Measured regularly, the PVload index indicates changes in inspiratory load imposed on the patient's respiratory system, such that the pressure/flow/volume assist delivered by the mechanical ventilator can be regulated to either increase assist to compensate for increased inspiratory load, or decrease assist in case of decreased inspiratory load.

The adjusting module 116 can be used to implement the changes in ventilatory assist, and several approaches can be used.

One possible choice is to relate the inspiratory load (PVload index) to the total pressure effort $(Paw_{tot})$ i.e. the pressure delivered by the mechanical ventilator plus the inspiratory pressure generated by the patient. The inspiratory pressure generated by the patient Ppat can be estimated by multiplying the index for ability to generate force (i.e. the ratio $Paw_{occ}/EAim_{occ}$ during airway occlusion) by the EAim during the inspiratory phase of a breath (with or without ventilatory assist), which provides a value for Paw during each breath (i.e. $Paw_{occ}/EAim_{occ}*EAim=Paw$) referred to as Ppat.

The pressure delivered by the mechanical ventilator Pvent and the tidal inspiratory volume Vt can be measured during each unoccluded breath. The total inspiratory pressure generated by the patient and the ventilator $Paw_{tot}$ is calculated by subtracting Ppat from Pvent (actually results in an addition of the pressures since Ppat is a negative value).

The total inspiratory pressure generated by the patient and the ventilator $Paw_{tot}$ is then divided by the inspiratory volume $(Paw_{tot}/Vt)$ of the same breath as $Paw_{tot}$ was obtained from, expressing the total inspiratory pressure generated by the patient and the ventilator relative to volume that will subsequently be referred to as PVinsp index.

Finally, if the PVload index (i.e. Paw/Vt as calculated above to describe the inspiratory load imposed on the patient's respiratory system) is expressed in relation to the PVinsp index $(Paw_{tot}/Vt)$ i.e. using the relation $(Paw/Vt)/(Paw_{tot}/Vt)$, a ratio expressing the estimated inspiratory load imposed on the patient's respiratory system in relation to the estimated total inspiratory pressure generated by the patient and the ventilator for that breath. This latter unloading index will be referred to as the UL index. A UL index of −1 indicates that the patient is not receiving any ventilatory assist, a UL index of −0.5 suggests equal pressure generation per volume between patient and ventilator, and a UL index of 0 indicates that the patient is completely unloaded.

Figure 4:
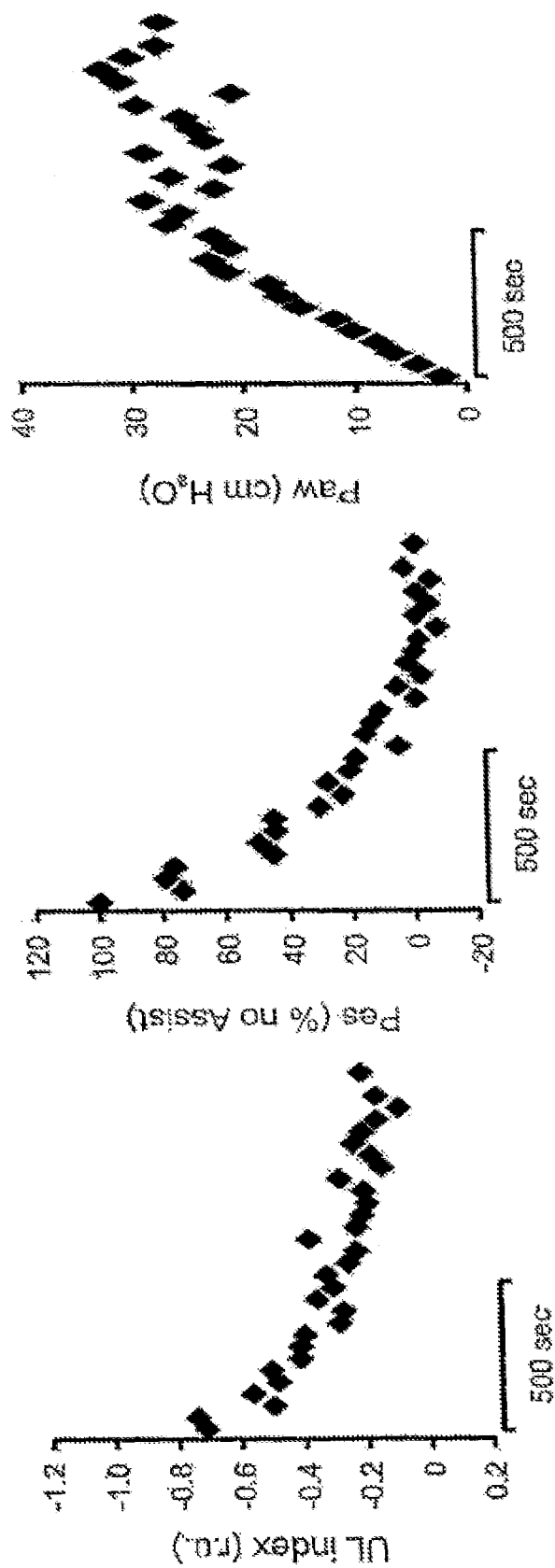
FIG. 4 are graphs showing the effect of ramp increase of ventilatory assist (Paw) on a UL index and measured unloading (Pes expressed in % of unassisted conditions), during neurally adjusted ventilatory assist.

Reference is now made to FIG. 4, which depicts graphs showing the effect of ramp increase of ventilatory assist (Paw) on the UL index and measured unloading (Pes expressed in % of unassisted conditions) during neurally adjusted ventilatory assist (U.S. Pat. No. 5,820,560). FIG. 4 shows a similarity of the UL index and measured unloading (Pes), with increasing ventilatory assist. Of course this UL index could be applied to any other mode of delivering ventilatory assist.

Another simpler approach to adjust ventilatory assist is to use absolute units to provide the amount of inspiratory airway pressure per volume that is predicted by the PVload index. For example if the PVload index is −50 cm $H_2O$/L and a required tidal volume is 0.5 L, the application of 25 cm $H_2O$ should theoretically suffice to compensate for the inspiratory load imposed on the patient's respiratory system during a tidal volume of 0.5 L. Hence, if the PVload index is less negative (e.g. to −40 cm $H_2O$/L) the ventilatory assist should be decreased (to 20 cm $H_2O$) to support a breath with tidal volume of 0.5 L and vice versa. If higher or lower compensation is required, a constant could be applied in the calculation which if being lower than 1 will provide less assist than originally estimated by the PVload index, or if higher than 1 will provide more assist.

All variables $Paw_{occ}$ and $EAim_{occ}$ during occlusion and Vt and EAim during patient's ventilator unassisted effort, or Paw and EAim during ventilator assisted efforts can be calculated as differences between onset and peak of the respective variables or as mean deflections of the respective variables. As well, the ratios Vt/EAim as well as $Paw_{occ}/EAim_{occ}$ can be obtained and compared at any point given that EAim is not decreasing. Other methods of calculating deflections, integrals, or related values could alternatively be used without departing from the scope of the present method and system. Moreover, the indices described hereinabove can be applied in all modes of mechanical ventilation given that the patient is making inspiratory efforts and parameters such as EAim, Paw and Vt are measured.

Figure 5:
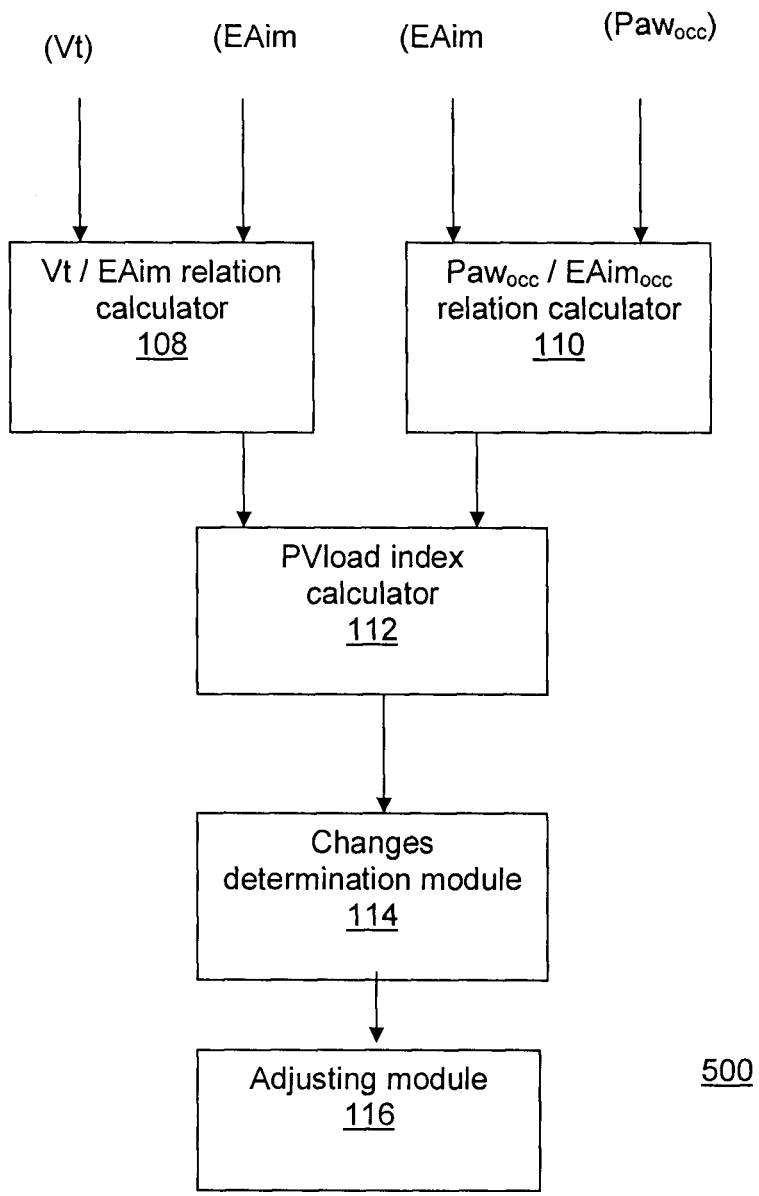
FIG. 5 is a schematic representation of another aspect of the system for measuring changes in inspiratory load during mechanical ventilation.

Reference is now made to FIG. 5, which is a schematic representation of another aspect of the system 500 for measuring changes in the inspiratory load. In this aspect, the inspiratory volume measurement Vt, the electrical activity of inspiratory muscle measurement (EAim and $EAIM_{occ}$) and the inspiratory airway pressure measurement $Paw_{occ}$ are measured by the mechanical ventilator and provided to the system 500. The system 500 could thus be added to a mechanical ventilator (not shown), or separate there from.

The calculators 108, 110 and 112 may be embodied in separate calculators and integrated into a single calculator. The calculators 108 may be implemented as hardware, such as for example in one or several Field Programmable Gate Arrays, or software being executed by a microprocessor. The changes determination module 114 and the adjusting module 116 may also be implemented in hardware or software. The changes determination module 114 may further comprise a memory for storing previous PVload indexes and determine trends there from. The memory of the changes determination module 114 may further store the trends.

Although the present method and system have been described by means of exemplary embodiments, modifications and changes made to those embodiments may fall within the scope of protection sought as described in the appended claims.

What is claimed is:

1. A method implemented in a mechanical ventilator for adjusting ventilator assist to a patient, comprising:
   measuring electrical activity EAim of at least one respiratory muscle of the patient during patient's inspiratory effort without causing an inspiratory occlusion in the patient;
   measuring an inspiratory volume Vt during patient's inspiratory effort without causing an inspiratory occlusion in the patient;
   measuring electrical activity $EAim_{occ}$ of the at least one respiratory muscle of the patient, while causing an inspiratory occlusion in the patient;
   measuring an inspiratory airway pressure $Paw_{occ}$, while causing an inspiratory occlusion in the patient;
   calculating a first relation between the measured inspiratory airway pressure $Paw_{occ}$ and the measured electrical activity $EAim_{occ}$;
   calculating a second relation between the measured inspiratory volume Vt and the measured electrical activity EAim;
   calculating a load index from the first and second relations;
   determining changes in inspiratory load imposed on the patient's respiratory system in relation to the load index; and
   adjusting the mechanical ventilator based on the determined changes in the inspiratory load to thereby adjust ventilator assist to the patient.

2. The method of claim 1, wherein the measured electrical activity EAim is an electrical activity of the patient's diaphragm EAdi.

3. The method of claim 1, wherein the measured inspiratory airway pressure $Paw_{occ}$ is an esophageal pressure.

4. The method of claim 1, wherein the inspiratory volume Vt is measured during an inspiration without ventilatory assist from the mechanical ventilator.

5. The method of claim 1, wherein the inspiratory airway pressure $Paw_{occ}$ and the electrical activity $EAim_{occ}$ are measured concurrently during an inspiration without ventilatory assist from the mechanical ventilator.

6. The method of claim 1, wherein the inspiratory volume Vt and the electrical activity EAim are concurrently measured during an unassisted inspiratory effort.

7. The method of claim 1, wherein the load index is $(Paw_{occ}/EAim_{occ})/(Vt/EAim)$.

* * * * *